United States Patent
Hu et al.

(10) Patent No.: US 6,210,924 B1
(45) Date of Patent: Apr. 3, 2001

(54) OVEREXPRESSING CYCLIN D 1 IN A EUKARYOTIC CELL LINE

(75) Inventors: Shaw-Fen Sylvia Hu; Jean Marie Gudas, both of Thousand Oaks; David William Brankow, Canoga Park, all of CA (US)

(73) Assignee: Amgen Inc., Thousand Oaks, CA (US)

( * ) Notice: Subject to any disclaimer, the term of this patent is extended or adjusted under 35 U.S.C. 154(b) by 0 days.

(21) Appl. No.: 09/371,309

(22) Filed: Aug. 10, 1999

Related U.S. Application Data (60) Provisional application No. 60/096,086, filed on Aug. 11, 1998.

(51) Int. Cl.[7] ............................. C12N 5/00; C12N 5/06; C12P 21/06
(52) U.S. Cl. ................ 435/69.1; 435/325; 435/358
(58) Field of Search ............................. 435/69.1, 325, 435/410, 468, 455, 254.11; 530/350

(56) References Cited

U.S. PATENT DOCUMENTS

| | | | |
|---|---|---|---|
| 4,703,008 | 10/1987 | Lin | 435/360 |
| 5,514,571 | 5/1996 | Riabowol | 435/461 |
| 5,744,314 | 4/1998 | Menzel et al. | 435/7.2 |

FOREIGN PATENT DOCUMENTS

| | | |
|---|---|---|
| WO 86/07594 | 12/1986 | (WO) . |
| WO 88/03808 | 6/1988 | (WO) . |

(List continued on next page.)

OTHER PUBLICATIONS

Diamond et al. (1981), "Monoclonal Antibodies: A New Technology for Producing Serologic Reagents" *The New England Journal of Medicine* 304:1344–1349.

Maxam and Gilbert (1977), "A new method for sequencing DNA" *Proc. Natl. Acad. Sci. USA* 74(2):560–564.

Nelles et al. (1987), "Characterization of a Fusion Protein Consisting of Amino Acids 1 to 263 of Tissue–type Plasminogen Activator and Amino Acids 144 to 411 of Urokinase–type Plasminogen Activator" *The Journal of Biological Chemistry* 262(22):10855–10862.

Ohtsubo & Roberts (1992), "Cyclin–Dependent Regulation of $G_1$ in Mammalian Fibroblasts" *Science* 259:1908–1912.

Okayama and Berg (1983), "A cDNA Cloning Vector That Permits Expression of cDNA Inserts in Mammalian Cells" *Molecular and Celleular Biology* 3(2):280–289.

Quelle et al, (1993), "Overexpression of mouse D–type cyclins accelerates $G_1$ phase in rodent fibroblasts" *Genes & Development* 7:1559–1571.

(List continued on next page.)

*Primary Examiner*—Robert A. Schwartzman
*Assistant Examiner*—Katharine F Davis
(74) *Attorney, Agent, or Firm*—Timothy J. Gaul; Ron K. Levy; Steven M. Odre

(57) ABSTRACT

The invention concerns eukaryotic cells useful in protein expression comprising (a) an inserted nucleic acid encoding a cyclin D gene product and (b) an inserted nucleic acid encoding a protein of interest, wherein the cyclin D gene product and the protein of interest are expressed in the cell. The invention also concerns a process for producing a protein of interest, which comprises (a) inserting into a eukaryotic cell a nucleic acid encoding a cyclin D gene product and a nucleic acid encoding a protein of interest; (b) culturing the cell under conditions permitting the expression of the protein of interest; and (c) isolating the protein of interest. The cells are preferably mammalian, with CHO cells most preferred. The cyclin D gene product is preferably of human origin. Suitable proteins of interest include erythropoietin (EPO), osteoprotegerin (OPG), OPG-Fc, leptin, Fc-leptin, and Novel Erythropoiesis Stimulating Protein (NESP).

18 Claims, 8 Drawing Sheets

FOREIGN PATENT DOCUMENTS

| | | |
|---|---|---|
| WO 91/05867 | 5/1991 | (WO) . |
| WO 94/09257 | 4/1994 | (WO) . |
| WO 95/16774 | 6/1995 | (WO) . |
| WO 96/05309 | 2/1996 | (WO) . |
| WO 96/40912 | 12/1996 | (WO) . |
| WO 97/06816 | 2/1997 | (WO) . |
| WO 97/18833 | 5/1997 | (WO) . |
| WO 97/23614 | 7/1997 | (WO) . |

OTHER PUBLICATIONS

Resnitzky et al., (1994), "Acceleration of the $G_1$/S Phase Transition by Expression of Cyclins D1 and E with an Inducible System" *Molecular and Cellular Biology* 14(3):1669–1679.

Sanger et al. (1977), "DNA sequencing with chain–terminating inhibitors" *Proc. Natl. Acad. Sci. USA* 74(12):5463–5467.

Urlaub et al (1980), "Isolation of Chinese hamster cell mutants deficient in dihydrofolate reductase activity": *Proc. Natl. Acad. Sci. USA* 77(7):44614220.

Zhou et al. (1996), "Overexpression of Cyclin D1 Enhances Gene Amplification" *Cancer Res.* 56:36–39.

Zieg et al., Properties of single–step mutants of syrian hamster cell lines resistant to N–(phosphonacetyl)–L–aspartate, Mol. Cell. Biol. 3: 2089–2098, 1983.*

Ewen et a l., Cell 73: 487–497, Functional interactions of the retinoblastoma protein with mammalian D–type cyclins, May 1993.*

Hiari and Sherr, Mol. Cell. Biol. 16:6457–6467, Interaaction of D–type cyclins with a novel myb–like transcription factor, DMP1, Nov. 1996.*

* cited by examiner

FIG. 1A  FIG. 1B

AM-1 CHOd-

Spinner harvests

FIG. 8B

Bioreactor harvests

OVEREXPRESSING CYCLIN D 1 IN A EUKARYOTIC CELL LINE

This application claims benefit to U.S. provisional 60/096,086 filed Aug. 11, 1998.

BACKGROUND OF THE INVENTION

Progression through the mammalian cell cycle is driven by orderly activation of cyclin-dependent kinases (CDKs). An active CDK is composed of a catalytic subunit and a regulatory subunit called cyclin. CDK activity is regulated through interactions with cyclins and CDK inhibitors (CKIs) and by post-translational modifications (e.g., phosphorylation).

Transition between cell cycle states is regulated at defined checkpoints by different cyclin subunits: G1 cyclins for the G1/S transition, S cyclins for progression through S phase, and G2 or mitotic cyclins for entry into mitosis. The commitment of a cell to enter the S phase occurs at a restriction point (R) late in G1, after which mitogenic growth factors are no longer required for cells to complete division.

Cyclins D and E are synthesized sequentially during G1 and are rate-limiting for S-phase entry, so they can be viewed as G1 cyclins. At least three mammalian genes encode D-type cyclins (D1, D2 and D3). D-type cyclins are progressively induced as part of the delayed early response to mitogenic stimulation, and they are expressed in a cell lineage-specific fashion. Assembly of D-type cyclins with CDK4 and CDK6 is regulated post-translationally by mitogens. Once assembled, cyclin D-bound CDKs must be phosphorylated by a CDK-activating kinase (CAK) to acquire catalytic activity.

Cyclin D genes are on a different branch of the evolutionary tree from A-, B-, or E-type cyclin, and D-type cyclins have some different properties from other cyclins. They are short-lived proteins ($t_{1/2}$<25 min). Withdrawal of growth factors during G1 prevents steady accumulation of cyclin D, correlating with the failure of growth factor-deprived cells to progress past the R point. Thus, expression of cyclin D is regulated by extracellular signals, unlike the periodic expression of cyclins A, B and E.

Overexpression of human cyclins D1 and E in rodent or human fibroblasts shortens G1, decreases cell size, and reduces the serum requirement for the G1-to-S transition (Resnitzky et al, *MCB*, 4 1669–79 (1994); Quelle etal., *Genes & Development* 7, 1559–71 (1993); Ohtsubo & Roberts, *Science* 259, 1908–12 (1992)). These results suggest that D cyclins might override a function physiologically regulated by cyclin E or vice-versa. However, overexpression of cyclin D or E does not lead to fibroblast transformation—cells remain serum-dependent, contact-inhibited, and unable to form colonies in semisolid medium. Overexpression of cyclin D1 has also been found to enhance endogenous gene amplification, suggesting that it plays a role in genomic instability during tumor development. Zhou et al., *Cancer Res.* 56: 36–9 (1996).

SUMMARY OF THE INVENTION

The present invention concerns a eukaryotic cell comprising:

(a) a cyclin D gene product, wherein the cyclin D gene product is functionally expressed in the cell at a level greater than any native level of expression; and (b) a protein of interest, wherein the protein of interest is expressed in the cell at a level greater than any native level of expression.

The present invention also concerns a process for producing a protein of interest, which comprises:

A. creating a eukaryotic cell that expresses
  1. a cyclin D gene product at a level greater than any native level of expression and
  2. a protein of interest at a level greater than any native level of expression;

B. culturing the cell under conditions permitting expression of the protein of interest and functional expression of the cyclin D gene product; and C. isolating the protein of interest.

The cells of this invention are preferably mammalian, with CHO cells most preferred. The cyclin D gene product is preferably mammalian, with human origin most preferred. The cyclin D gene or the gene encoding the protein of interest (or both) may be comprised in an expression vector or vectors inside the cell or may be integrated into the cell genome.

Any number of proteins of interest may be used in the present invention. Specifically, EPO, OPG, leptin and NESP, and any derivatives thereof may be employed.

DETAILED DESCRIPTION OF THE INVENTION

The following definitions apply to terms as used throughout this specification, unless otherwise limited in specific instances.

The terms "inserted" and "inserting" of nucleic acids mean that the nucleic acid is introduced into a cell or organism by external methods (e.g., transfection). The inserted nucleic acid may have a sequence foreign to or already present in the cell's genome. In the latter case, the inserted nucleic acid enables greater or differentially regulated expression of the protein encoded by the inserted nucleic acid.

The term "EPO-related protein" refers to erythropoietin and derivatives and analogues thereof that may be formed by recombinant DNA and other methods. Such derivatives include proteins having terminal truncations, removal of internal amino acids (e.g., by restriction and re-ligation of the associated DNA), amino acid substitutions and the like. Such derivatives also include fusion proteins (e.g., with an Fc region). Exemplary derivatives of erythropoietin are described in International patent applications WO 91/05867, 94/09257,88/03808, and 86/07594, each of which is hereby incorporated by reference.

The term "leptin-related protein" refers to leptin, preferably human leptin, and derivatives thereof that may be formed by recombinant DNA and other methods. Such derivatives include proteins having terminal truncations, removal of internal amino acids, amino acid substitutions, and the like. Also included within this definition are fusion proteins comprising leptin, such as a fusion protein comprising leptin and an Fc fragment. Suitable leptin derivatives are described in patent applications WO 96/40912 (filed Dec. 19, 1996), WO 96/05309 (filed Feb. 22, 1996), WO 97/06816 (filed Feb. 27, 1997), and WO 97/18833 (filed May 29, 1997), which are hereby incorporated by reference.

The term "OPG-related protein" refers to OPG and derivatives thereof that may be formed by recombinant DNA and other methods. Such derivatives include proteins having terminal truncations, removal of internal amino acids (e.g., by restriction and re-ligation of the associated DNA), amino acid substitutions and the like. Such derivatives also include fusion proteins (e.g., with an Fc region). Exemplary derivatives of OPG are described in International patent application WO 97/23614, which is hereby incorporated by reference.

Process of Preparation

Gene Constructs

The nucleic acids used in the present invention may be prepared by recombinant nucleic acid methods. See, for example, the recombinant DNA methods of Nelles et al., *J. Biol. Chem.*, 262, 10855 (1987).

The nucleic acids may be derived from a variety of sources, including genomic DNA, subgenomic DNA, cDNA, synthetic DNA, and combinations thereof. Genomic and cDNA may be obtained in a number of ways. Cells coding for the desired sequence may be isolated, the genomic DNA fragmented (e.g., by treatment with one or more restriction endonucleases), and the resulting fragments cloned, identified with a probe complementary to the desired sequence, and screened for the presence of a sequence coding for the desired activity. For cDNA, the cDNA may be cloned and the resulting clone screened with a probe for cDNA coding for the desired region. Upon isolation of the desired clone, the cDNA may be manipulated in substantially the same manner as the genomic DNA.

In addition to the coding sequence of the protein of interest, the gene construct should contain a number of regulatory regions. For expression, transcriptional and translational signals recognized by an appropriate host are necessary. The coding sequence should also be linked to a promoter compatible with the host cell. The promoter may be inducible, allowing further control of expression, or constitutive. A number of suitable promoters are known in the art.

Alternatively, the promoter region from genomic DNA may be obtained in association with the coding sequence. To the extent the host cells recognize the transcriptional regulatory and translational initiation signals associated with the coding region, the 5' region adjacent to the coding sequence may be retained and employed for transcriptional and translational regulation. This region typically will include those sequences involved with initiation of transcription and translation, such as the TATA box, capping sequence, CAAT sequence, and the like. Typically, this region will be at least about 150 base pairs long, more typically about 200 bp, and rarely exceeding about 1 to 2 kb.

The non-coding 3' region may be retained, as well, especially for its transcriptional termination regulatory sequences, such as the stop signal and polyadenylated region. In addition, the non-coding 3' region may also contain an enhancer. Where the transcriptional termination signals are not satisfactorily functional in the host cell, then a functional 3' region from a different gene may be substituted. The choice of the substituted 3' region would depend upon the cell system chosen for expression.

A wide variety of transcriptional and translational regulatory sequences may be employed, depending upon the nature of the host. The transcriptional and translational regulatory sequences may be derived from viral sources (e.g., adenovirus, bovine papilloma virus, Simian virus, and the like) where the regulatory signals are derived from a gene that has a high level of expression in the host. Alternatively, promoters from mammalian expression products (e.g., actin, collagen, myosin and the like) may be employed. Transcriptional initiation regulatory signals may be selected that allow for repression or activation, so that expression of the genes can be modulated. One such controllable modulation technique is the use of regulatory signals that are temperature-sensitive, so that expression can be repressed or initiated by changing the temperature. Another controllable modulation technique is the use of regulatory signals that are sensitive to certain chemicals.

The constructs may comprise a nucleic acid sequence endogenous to the host cell in conjunction with promoter, enhancer, and other regulatory regions that may or may not be endogenous to the cell. Such constructs enable expression of the endogenous sequence to be increased (e.g., through operable coupling to a constitutive promoter) or controlled (e.g., through operable coupling to regulatory signals).

To form the gene constructs, DNA fragments may be ligated in accordance with conventional techniques known in the art. Such techniques include use of restriction enzymes to convert sticky-ended fragments to blunt ends (or vice-versa), polymerases and nucleotides to fill in sticky ends to form blunt ends, alkaline phosphatase to avoid undesired ligations, and ligases to join fragments.

The constructs may be introduced into a cell by tranformation in conjunction with a gene allowing for selection where the construct will become integrated into the host genome (e.g., by homologous recombination). Usually, the construct will be part of a vector having a replication system recognized by the host cell.

Expression Vectors

Expression vehicles for production of the molecules of the invention include plasmids or other vectors. In general, such vectors contain control sequences that allow expression in various types of cells. Suitable expression vectors containing the desired coding and control sequences may be constructed using recombinant DNA techniques known in the art, many of which are described in Sambrook et al., *Molecular Cloning: A Laboratory Manual*, Second Edition, Cold Spring Harbor Laboratory, Cold Spring Harbor, N.Y. (1989).

An expression vector as contemplated by the present invention is at least capable of directing the replication and expression of the nucleic acid encoding the protein of interest or of the cyclin D gene product. One class of vectors utilizes DNA elements that provide autonomously replicating extrachromosomal plasmids derived from animal viruses (e.g., bovine papilloma virus, polyomavirus, adenovirus, or SV40). A second class of vectors relies upon the integration of the desired gene sequences into the host cell chromosome.

Expression vectors useful in the present invention typically contain an origin of replication, a promoter located 5' to (i.e., upstream of) the DNA sequence to be expressed, and a transcription termination sequence.

Suitable origins of replication include, for example, the ColE1, pSC101, M13, SV40 and EBV origins of replication. Suitable termination sequences include, for example, the bovine growth hormone, SV40, lacZ and AcMNPV polyhedral polyadenylation signals. Suitable promoters include, for example, the cytomegalovirus promoter, the lacZ promoter, the gal 10 promoter and the AcMNPV polyhedral promoter. The promoter sequence may also be inducible, to allow modulation of expression (e.g., by the presence or absence of nutrients or other inducers in the growth medium). One example is the lac operon obtained from bacteriophage lambda plac5, which can be induced by IPTG.

The expression vectors may also include other regulatory sequences for optimal expression of the desired product. Such sequences include stability leader sequences, which provide for stability of the expression product; secretory leader sequences, which provide for secretion of the expression product; enhancers, which upregulate the expression of the DNA sequence; and restriction enzyme recognition sequences, which provide sites for cleavage by restriction endonucleases. All of these materials are known in the art and are commercially available. See, for example, Okayama, *Mol. Cell Biol.*, 3,280 (1983).

A suitable expression vector may also include marking sequences, which allow phenotypic selection of transformed host cells. Such a marker may provide prototrophy to an auxotrophic host, biocide resistance (e.g., antibiotic resistance) and the like. The selectable marker gene can either be directly linked to the coding sequences to be expressed, or introduced into the same cell by co-transfection. Examples of selectable markers include genes for resistance to neomycin, ampicillin, hygromycin resistance and the like.

The characteristics of the actual expression vectors used must be compatible with the host cell to be employed. For a mammalian host, for example, the expression vector may contain promoters isolated from the genome of mammalian cells, (e.g., mouse metallothionine promoter), or from viruses that grow in these cells (e.g., vaccinia virus 7.5 K promoter).

Suitable commercially available expression vectors into which the coding sequences of the present invention may be inserted include the mammalian expression vectors pcDNA I or pcDNA I/Neo (which is preferred), the baculovirus expression vector pBlueBac, the prokaryotic expression vector pcDNA II and the yeast expression vector pYes2, all of which may be obtained from Invitrogen Corp., San Diego, Calif.

Host Cells

The present invention additionally concerns host cells containing expression vectors that comprise DNA sequences for the protein of interest and the cyclin D gene product. Suitable host cells are eukaryotic cells; for example, *Spodoptera frugiperda* insect cells, COS-7 cells, human fibroblasts, and *Saccharomyces cerevisiae* cells. Mammalian cells that may be useful as hosts include cells of fibroblast origin (e.g., VERO or CHO-K1) or lymphoid origin (e.g., SP2/0-AG14, or P3×63Sg8) or derivatives thereof. Preferred mammalian host cells are CHO cells.

Immortalized cells, such as myeloma or lymphoma cells, are also suitable host cells. These cells may be grown in an appropriate nutrient medium in culture flasks or injected into a synergenic host (e.g., mouse or rat) or an immunodeficient host or host site (e.g., nude mouse or hamster pouch). In particular, the cells may be introduced into the abdominal cavity for production of ascites fluid and harvesting of the chimeric molecule. Alternatively, the cells may be injected subcutaneously and the antibodies harvested from the blood of the host. The cells may be used in the same manner as the hybridoma cells. See Diamond et al., *N. Eng. J. Med.* 304,1344 (1981); *Monoclonal Antibodies: Hybridomas-A New Dimension in Biologic Analysis* (Kennatt, et al., eds.) Plenum (1980).

Expression vectors may be introduced into host cells by various methods known in the art. For example, transfection of host cells with expression vectors can be carried out by the calcium phosphate precipitation method. However, other methods for introducing expression vectors into host cells (for example, electroporation, liposomal fusion, nuclear injection, and viral or phage infection) can also be employed.

Host cells containing an expression vector may be identified by one or more of the following six general approaches: (a) DNA—DNA hybridization; (b) the presence or absence of marker gene functions; (c) assessing the level of transcription as measured by the production of mRNA transcripts encoding the gene constructs in the host cell; (d) detection of the gene product immunologically; (e) enzyme assay; and (f) PCR. These methods are well known in the art; see, for example, U.S. Pat. No. 5,744,314, which is hereby incorporated by reference.

The expression vectors and DNA molecules of the present invention may also be sequenced. Various sequencing methods are known in the art. See, for example, the dideoxy chain termination method described in Sanger et al., *Proc. Natl. Acad. Sci. USA* 74, 5463–7 (1977), and the Maxam-Gilbert method described in *Proc. Natl. Acad. Sci USA* 74,560–4 (1977).

Once an expression vector has been introduced into an appropriate host cell, the host cell may be cultured under conditions permitting expression of large amounts of the protein of interest. The protein of interest may be isolated and purified in accordance with conventional conditions, such as extraction, precipitation, chromatography, affinity chromatography, electrophoresis, and the like. The preferred method is affinity chromatography.

It should, of course, be understood that not all expression vectors and DNA regulatory sequences will function equally well to express the nucleic acids of the present invention. Neither will all host cells function equally well with the same expression system. However, one of ordinary skill in the art may make a selection among expression vectors, DNA regulatory sequences, and host cells using the guidance provided herein without undue experimentation and without departing from the scope and spirit of the present invention.

DETAILED DESCRIPTION OF PREFERRED EMBODIMENTS

Below are detailed descriptions of specific embodiments of the present invention. These embodiments are exemplary and serve to illustrate the broad applicability of the present invention. Unless otherwise indicated in the specification, these embodiments comprise preferred elements of the invention.

Materials & Methods

Plasmids

Human Cyclin D1 gene (Genbank access # M64349) was cloned into pcDNA 3.1 (Invitrogen) and expressed constitutively under the cytomegalovirus (CMV) promoter/enhancer to generate pcDNA 3.1/cyclin D1. The vector also carries the neomycin resistance gene for selection of stable mammalian cell lines in the presence of G418.

Cell culture

CHOd⁻(SF) cells were grown in 100 mm dishes in complete medium {DMEM (Gibco/BRL), 5% Fetal Bovine Serum (JRH Biosciences), 1% nonessential amino acids (Gibco/BRL), 1% hypoxanthine/thymidine (HT)(Gibco/BRL), and 1% glutamine/penicilin/streptomycin (Gibco/BRL)}. The cells were trypsinized, counted, and seeded in 60 mm plates (Falcon), at 1×10 e6 cells/dish. AM-1 CHOd⁻ cells were grown in suspension spinner culture in Amgen VM-soy medium. Cells were counted, centrifuged, resuspended in complete medium, and seeded in 60 mm plates at 1×10e6 cells/dish. Cells were incubated overnight. Three hours prior to transfection, the medium on the cells was replaced with 4 ml fresh medium.

Cyclin D1 Transfection

This transfection used the vector pcDNA3.1 neo® (Invitrogen) containing the cyclin D1 cDNA insert. For each 60 mm plate of cells, 5 ug of pcDNA3.1 /cyclin D1 (2 mg/ml) and 5 µg mouse genomic carrier DNA (Clontech) (100 µg/ml) were added to 172.5 µl sterile distilled water. Twenty-five microliters of 2.5 M $CaCl_2$ were added to the DNA solution, giving a final volume of 250 µl. As a vector control, 5 µg pneo vector DNA (1.126 mg/ml) together with 5 µg carrier DNA, were added to 170.5 pl sterile water, followed by 25 µl 2.5 M $CaCl_2$. As a mock control, 25 µl 2.5 M $CaCl_2$ was added to 225 µl water. The DNA solutions were added dropwise to an equal volume (250 µl) of 2×HBS (280 mM NaCl, 10 mM KCl, 1.5 mM $NaHPO_4$2 HO, 0.2 mM dextrose, 50 mM HEPES, pH 7.05), through which air was constantly bubbled. The DNA/HBS solutions were incubated at room temperature for 30 minutes. The medium was removed from the CHO cell plates and the DNA/HBS solutions (500 µl total volume per dish) were added dropwise. A total of 3 plates were treated with pcDNA3.1/cyclin D1, and one plate each for the vector and mock controls for each cell line. The cells were incubated at room temperature for 30 minutes, after which 5 ml of complete medium was added to each dish. The cells were then incubated overnight at 37° C. On the following day, the medium was replaced with fresh medium.

The CHO(SF) cells reached confluence 48 hours after the transfection. The cells were trypsinized and replated in complete medium at a ratio of 1×60 mm dish to 8×100 mm dishes. On the following day, the medium was replaced with complete medium containing 1 mg/ml Geneticin (G418) (Gibco/BRL). The AM-1 CHO cells reached confluence 72 hours after transfection, and were similarly replated. The medium on the cells was replaced with fresh complete medium +G418 twice weekly. Ten days after the initial addition of the G418 selective medium, colonies were isolated from the CHO(SF) and AM-1 CHO cyclin D1-transfected plates using glass cloning cylinders (Bellco). Cells were trypsinized and reseeded in 24-well plates. The transfection frequency of the CHO(SF) cells was much higher (>100 colonies/plate) than that of the AM-1 CHO cells (20–30 colonies/plate). A total of 72 colonies were isolated from the CHO(SF)/cyclin D1 plates, and 68 colonies from the AM-1 CHO/cyclin D1 plates. No colonies were present on either set of mock control dishes containing G418 selective medium. After colonies had been picked, the remaining cells from each set of plates were trypsinized and combined into pool cultures in 100 mm plates (3 pools for CHO(SF)/cyclinD1, and 2 pools for AM-1 CHO/cyclin D1).

The transfected cells were grown to confluence and then re-plated in 6 well plates, 2 wells per done/pool. Upon reaching confluence, one well of cells for each clone/pool was lysed with 250 ml 1% Triton lysis buffer (1% Triton ×100, 1 mM NaVO3, 50 mM Tris/HCl pH 8, 100 mM NaCl, protease inhibitors). Lysates were centrifuged at 14 K for 15 minutes. Supernatants were collected and stored at −20 ° C. Lysates were analyzed by western blot for cyclin D1 expression. 25 µl of each sample plus control samples of the parent CHO(SF) and AM-1 CHO lines, were mixed with 5 µl 5×PAGE gel sample buffer, boiled 3 minutes, and loaded on 12% Novex Tris-glycine gels. The gels were electroblotted onto 0.2µ nitrocellulose filters (Schleicher and Schuell). The filters were probed with anti-cyclin D1 Ab-3 monoclonal antibody (Calbiochem) and developed using Amersham ECL reagents. Results indicated varying degrees of overexpression of cyclin D1 in the pool cultures and most of the clones.

The two AM-1 CHO/cyclin D1 pool cultures and the two highest expressing CHO(SF)/cyclin D1 pool cultures were combined into "master pools" for each cell line to be used in subsequent transfections. The master pool cultures were tested to determine if they had retained the DHFR negative phenotype by growing the cells in hypoxanthine/thymidine-free selective medium (DMEM, 5% dialyzed fetal bovine serum (Hyclone), non-essential amino acids, glutamine/penicillin/streptomycin). No cell growth was detected in this medium.

EPO Transfection

Master pool cultures of CHO(SF)/cyclin D1 and AM-1 CHO/cyclin D1 were maintained in complete CHOd⁻ medium supplemented with 1 mg/ml G418. These cells were seeded in 60 mm plates at 8×10 e5 cells/dish and incubated overnight. The cells were transfected using the above protocol with pSW19 (a close derivative of pDSRα2)/EPO target DNA, pDSRα2 vector control DNA, and herring sperm carrier DNA (Gibco/BRL). A final concentration of 5 µg/dish of pSW19/EPO DNA was used. Twenty-four hours after transfection, the cells were given fresh medium. Seventy-two hours after transfection, the cells were trypsinized and replated into selective medium+1 mg/ml G418 at a ratio of 1:8, 1:10, and 1:20 (60 mm plate to 100 mm plates). Medium on the cells was replaced twice weekly with fresh medium containing G418. Twelve days after replating, 48 colonies were isolated from the CHO(SF)/cyclin D1/EPO-transfected plates. The remaining cells were trypsinized and combined into two pool cultures. Fifteen days after replating, 48 colonies were isolated from the AM-1 CHO/cyclin D1/EPO-transfected plates, and the remaining cells were combined into two pools. EPO expression was analyzed by western blot on serum-free conditioned medium harvests from confluent 24-well cultures of isolated clones or 100 mm plate cultures of the pools. Gels were run under reducing conditions, and blots were probed with anti-EPO monoclonal antibody 2D8.

OPG Transfections

Transfections of pSW19/OPG DNA construct into CHOd⁻ (SF)/cyclin D1 and AM-1 CHOd⁻/cyclin D1 master pools, and the CHOd⁻ (SF) parent line were carried out in the same manner as the EPO transfections. Two separate transfections of OPG-Fc (22-201) were carried out into all three host cell lines. A total of 124 CHO(SF), 110 CHO (SF)/cycD, and 147 AM-1 CHO/cycD colonies were picked from the OPG-Fc (22-201) transfections. OPG expression was analyzed in the resulting clones and pools by western blot using anti-huIgG-Fc-HRP antibody (Pierce), or affinity-purified rabbit polyclonal anti-huOPG.

Propidium Iodide Staining for DNA

Cells were seeded in 100 mm plates and allowed to grow to approximately 50% confluence. Cells must be in log phase for the assay. The cells were harvested by trypsinization and pipetted into a centrifuge tube containing an equal volume of DMEM/FBS. An aliquot of the cell suspension was counted with a hemocytometer. Cell density should be approximately $10^6$–$10^7$ cells/5 ml. The cells were pelleted by centrifugation at 1000×g and washed twice with ice cold PBS. The cells must be in a single-cell suspension. 0.5 ml PBS was added and the cell suspension was vortexed. The cells were then fixed by adding 2 ml of 70% ethanol dropwise down the side of the tube while mixing the cell suspension gently. The minimum fixing time is 30 minutes. (At this point the cell suspension can be stored for about 2 weeks at 4° C. before staining and analysis.) The cells were centrifuged to remove the ethanol supernatant, washed once with PBS and allowed to rehydrate for 5 minutes at 4° C. The cells were centrifuged, the PBS was removed, and the pellet was resuspended in 0.5 ml propidium iodide solution (Molecular Probes) (50 µg/ml prepared in PBS). 10 µl of DNase-free RNase (10 mg/ml) (Boehringer Mannheim) was added and the cell suspension was incubated at 37° C. for 20 minutes. The samples were diluted with 1 ml of PBS and were analyzed by FACS within 1 hour.

Gene Amplification

Gene amplification in the cells was carried out by the gradual step-wise addition of methotrexate (MTX) to the growth medium. The cells were subcultured at a ratio of 1:10 in 100 mm plates in three low concentrations of methotrexate (1 nM, 2.5 nM, and 5 nM). The growth of the cells was monitored and the plate which reached confluence first was used for the next round of amplification. If the cells grew equally well in more than one concentration of methotrexate, the highest concentration was used for the next round. A 48-hour serum-free DMEM harvest (4 ml/plate) was taken for analysis of the protein expression level by western blot or EIA. The cells were allowed to recover in complete medium with methotrexate for 24 hours and then subcultured at a 1:10 ratio into 3 higher methotrexate concentrations. The concentration of MTX was increased in increments of 10 nM up to 100 nM. In general, if the protein expression level has not reached a peak by 100 nM, amplification is continued in increments of 100 nM until a maximum expression level is reached. The cells were maintained in the presence of MTX once the optimal concentration had been determined.

Generation of AM-1/D cell line

Figure 1A:
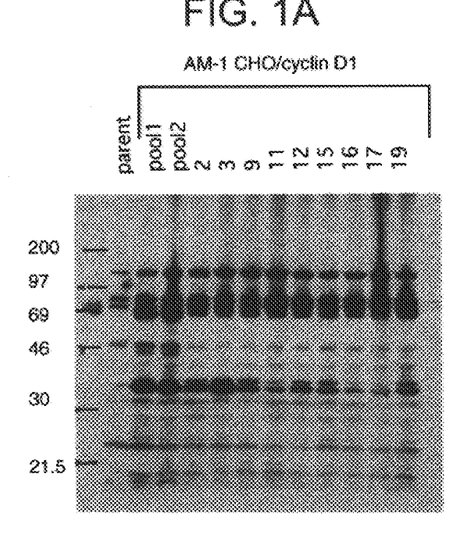
FIGS. 1A and 1B show a western blot of lysates of AM-1 cells transfected with pcDNA3.1/cyclin D1 and treated with a human cyclin D1-specific antibody (see Materials and Methods). This blot demonstrates the expression of human cyclin D1 in the AM-1/D cells.
Figure 1B:
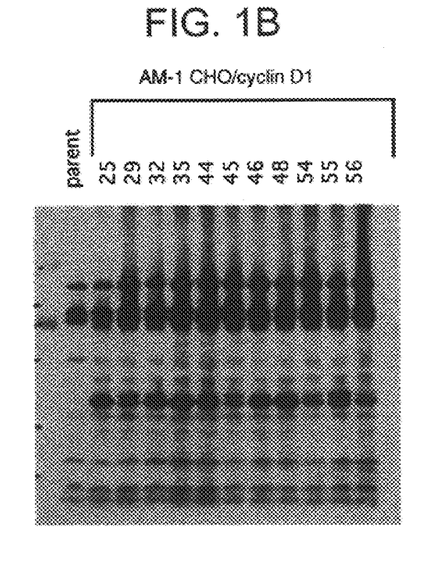
Figure 2A:
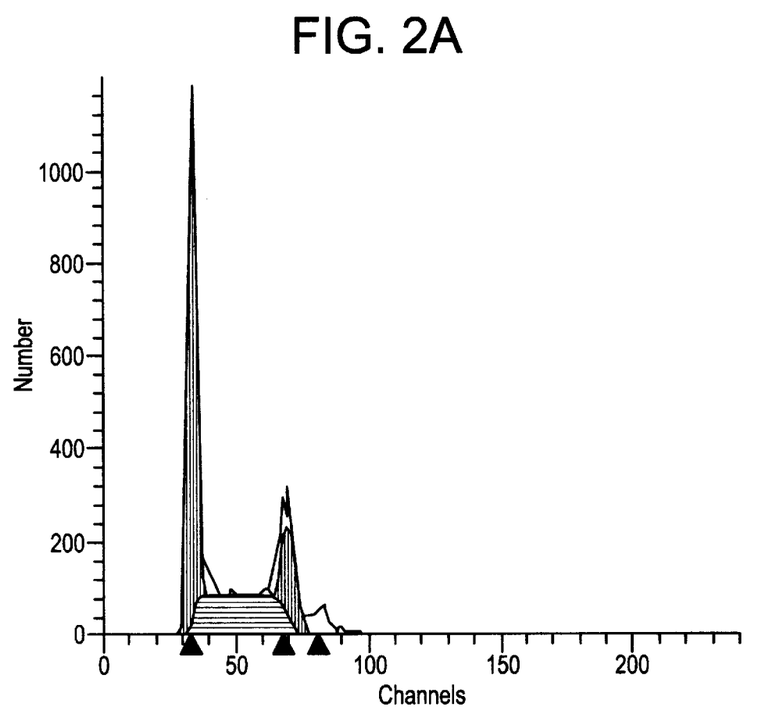
FIGS. 2A, 2B, 2C, and 2D are histograms showing the relative DNA content (x axis) and cell number (y axis) of unsynchronized cells from the AM-1/D and AM-1 cell lines stained with propidium iodide and analyzed by FACScan (Becton Dickinson; see Materials and Methods). These figures show that there were significantly more cells in the S phase in the AM-1/D cells.
Figure 2B:
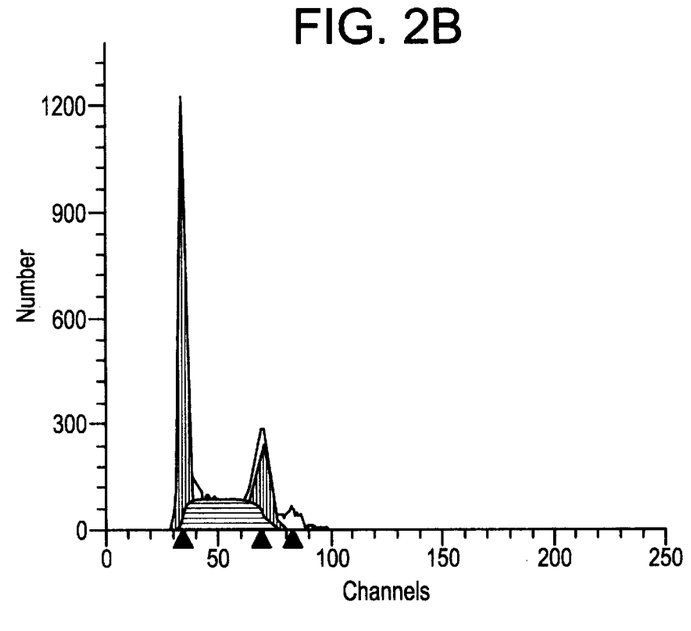
Figure 2C:
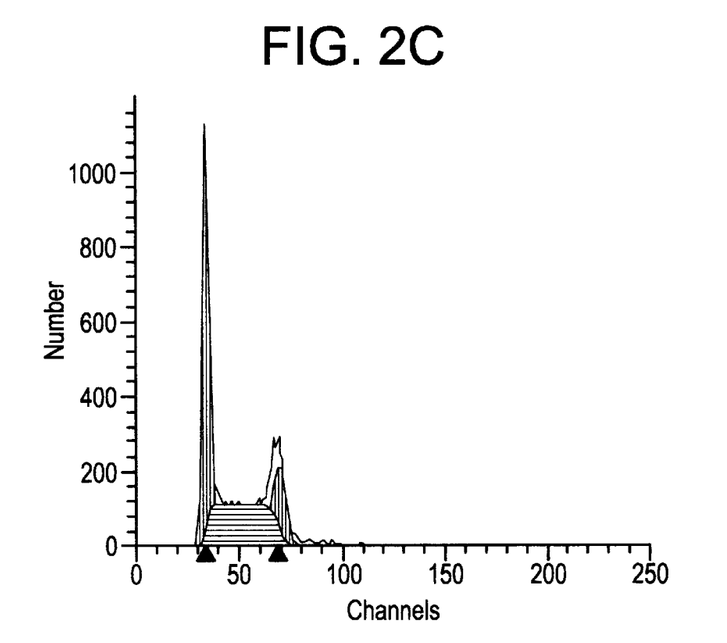
Figure 2D:
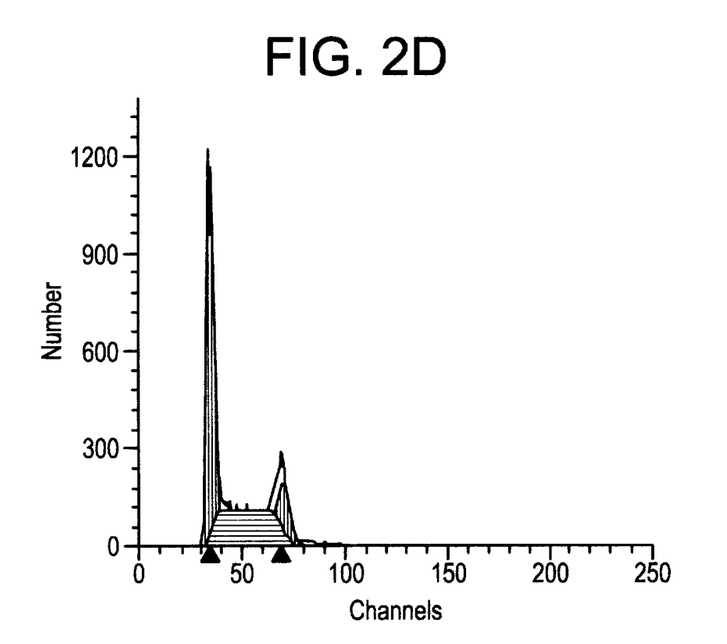

The AM-1/D cell line was derived from the CHOd(−) cell line described in U.S. Pat. No. 4,703,008, issued Oct. 27, 1987 and Urlaub et al. (1980), *Proc. Natl. Acad. Sci.* 77:4461, both of which are hereby incorporated by reference. The CHOd(−) cell line was adapted through passaging in the VM-SOY media with diminishing levels of and finally total absence of fetal bovine serum. The resulting serum-free adapted cell line AM-1 still retains the dhfr(−) phenotype. The AM-1 cell line was engineered to over-express human cyclin D1.

pcDNA3.1/cyclin D1 was transfected into the AM-1 cell line by the standard calcium phosphate precipitation procedure for transfection. Upon selection with G418, the colonies were trypsinized and combined into two pools. The expression of human cyclin D1 protein was demonstrated by Western blots (FIGS. 1A and 1B) of the cell lysates prepared from the pools using a human cyclin D1 specific antibody (anti cyclin D1 Ab-3, Calbiochem). A number of colonies were randomly picked with cloning rings and the cell lysates prepared and analyzed as well. The expression of human cyclin D1 was variable among the clones as expected. In comparison with the clones, the two pools exhibited overall high levels of human cyclin D1 protein (FIG. 1). The two pools were combined into a master pool culture (AM-1/D), which was the parent cell line used in all subsequent experiments.

Human cyclin D1 expressed in AM-1/D cell line is functional

We determined that human cyclin D1 was functionally expressed by its alteration of cell cycle dynamics; see, for example, FIG. 2 and below.

Unsynchronized cells from AM-1/D and AM-1 cell lines were stained with propidium iodide and analyzed by FAC-Scan (Becton Dickinson). FIGS. 2A–2D show relative DNA content (x axis) and cell number (y-axis). There were significantly more cells in the S-phase for the AM-1/D cells (40.08%, 40.14%) compared to the AM-1 cells (33.73%, 32.25%). This demonstrated that overexpression of human cyclin D1 in the AM-1/D, a CHO cell line, was functional as to alter the cell cycle dynamics significantly.

Example 1

Plasmid pDSRα2/OPG-Fc was constructed to express a human OPG (GenBank access # U94332 )-Fc fusion protein with the expression vector pDSRα2. Using standard calcium phosphate precipitation, linearized DNA of pDSRα2/OPG-Fc was transfected in parallel into AM-1/D cells and unmodified, original AM-1 cells. 44 colonies from each transfection were picked randomly after cells were placed in selective media lacking the HT supplements for two weeks.

Figure 3:
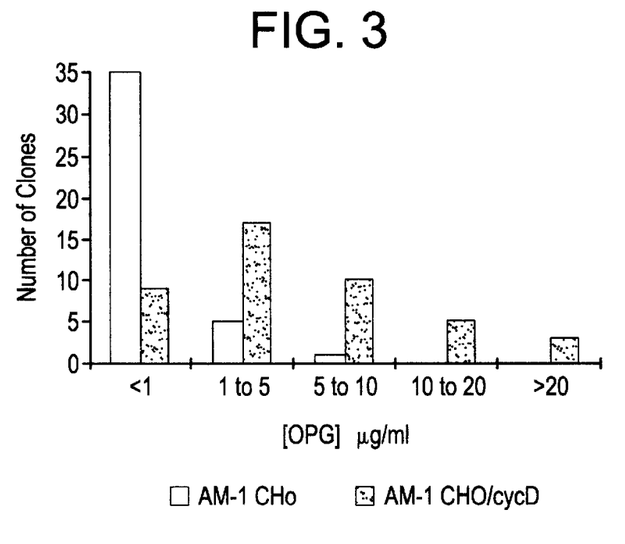
FIG. 3 is a graph showing the number of clones expressing OPG-Fc at various levels. AM-1/D cells were transfected with plasmid pDSRαt2/OPG-Fc as described in Example 1 hereinafter. This graph shows that the highest expressing clones were derived from the AM-1/D cell line.

The colonies were transferred individually into 24-well plates and grown to confluency. After 48 hours, serum-free conditioned media were collected and analyzed by EIA using antiserum specific for human OPG. FIG. 3 shows the number of clones expressing OPG-Fc at various levels from these two cell lines. It is clear that there are significantly more clones from the AM-1/D cell lines expressing higher levels of the recombinant protein, and that all of the highest expressing clones that expressed more than 20 mg/ml OPG-Fc were derived from the AM-1/D cell line.

Example 2

Figure 4:
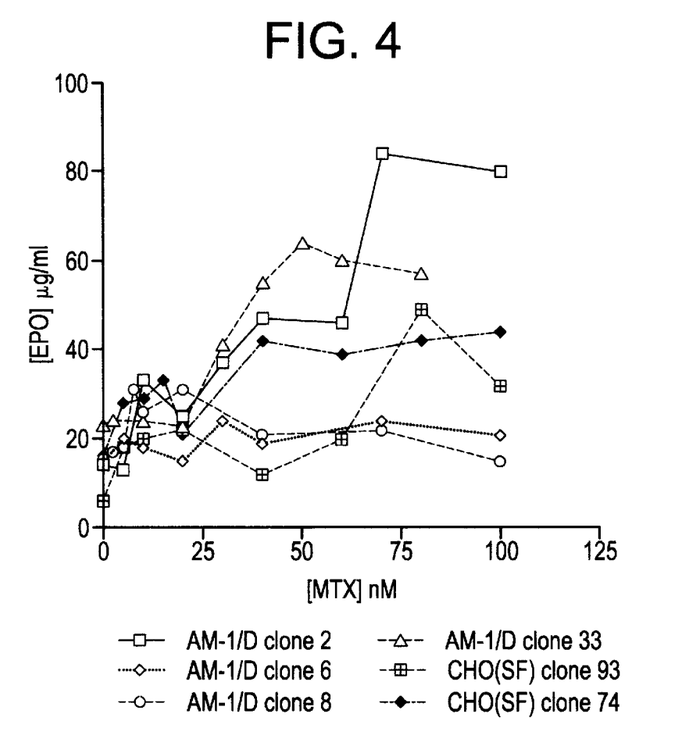
FIG. 4 is a graph showing the expression of EPO plotted against the concentration of MTX used for amplification. AM-1 /D cells were transfected with plasmid pDSRα2/hEPO as described in Example 2 hereinafter. Two of the clones exhibited elevated EPO production with increasing concentrations of MTX, demonstrating successful gene amplification.

Plasmid pDSRa2/hEpo was constructed to express the human Epo gene and transfected into AM-1/D cells following the calcium phosphate method described above. Forty-eight colonies were picked randomly for further analysis. Four of the high expressing clones were identified by EIA analysis of the conditioned media and subjected to methotrexate amplification starting at 1 nM. FIG. 4 shows the expression of EPO during the process of amplification. Two of the clones, AM-1/D clone 2 and AM-1/D clone 33 exhibited elevated Epo production with increasing concentrations of MTW, demonstrating successful gene amplification. These clones were tested upon freeze-and-thaw, and extensive passages with no loss of Epo expression demonstrating the stability of the Epo gene expression in these clones.

Expression of OPG in AM-1/cyclin D CHO cells

Figure 5:
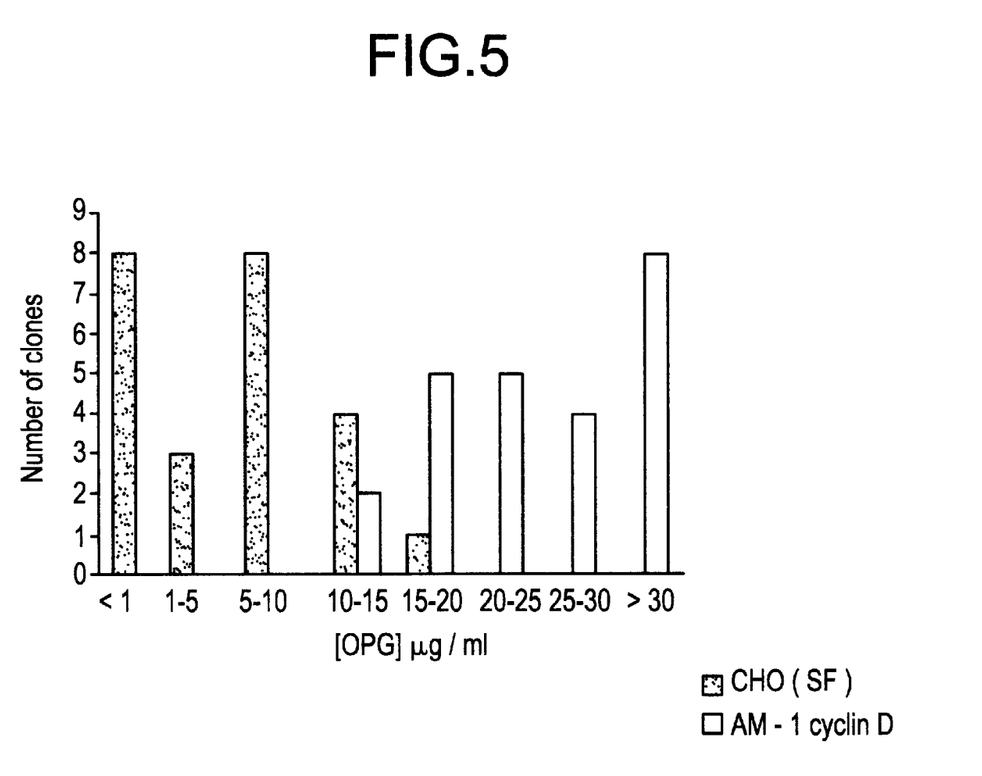
FIG. 5 shows a comparison of OPG(22-194)-cys-Fc expression levels in 46 individual clones derived from AM-1 CHO cells or AM-1/cyclin D CHO cells. Clones derived from the AM-1/cyclin D CHO cell line show significantly higher levels of expression of OPG(22-194)-cys-Fc than clones derived from AM-1 CHO cells.
Figure 6:
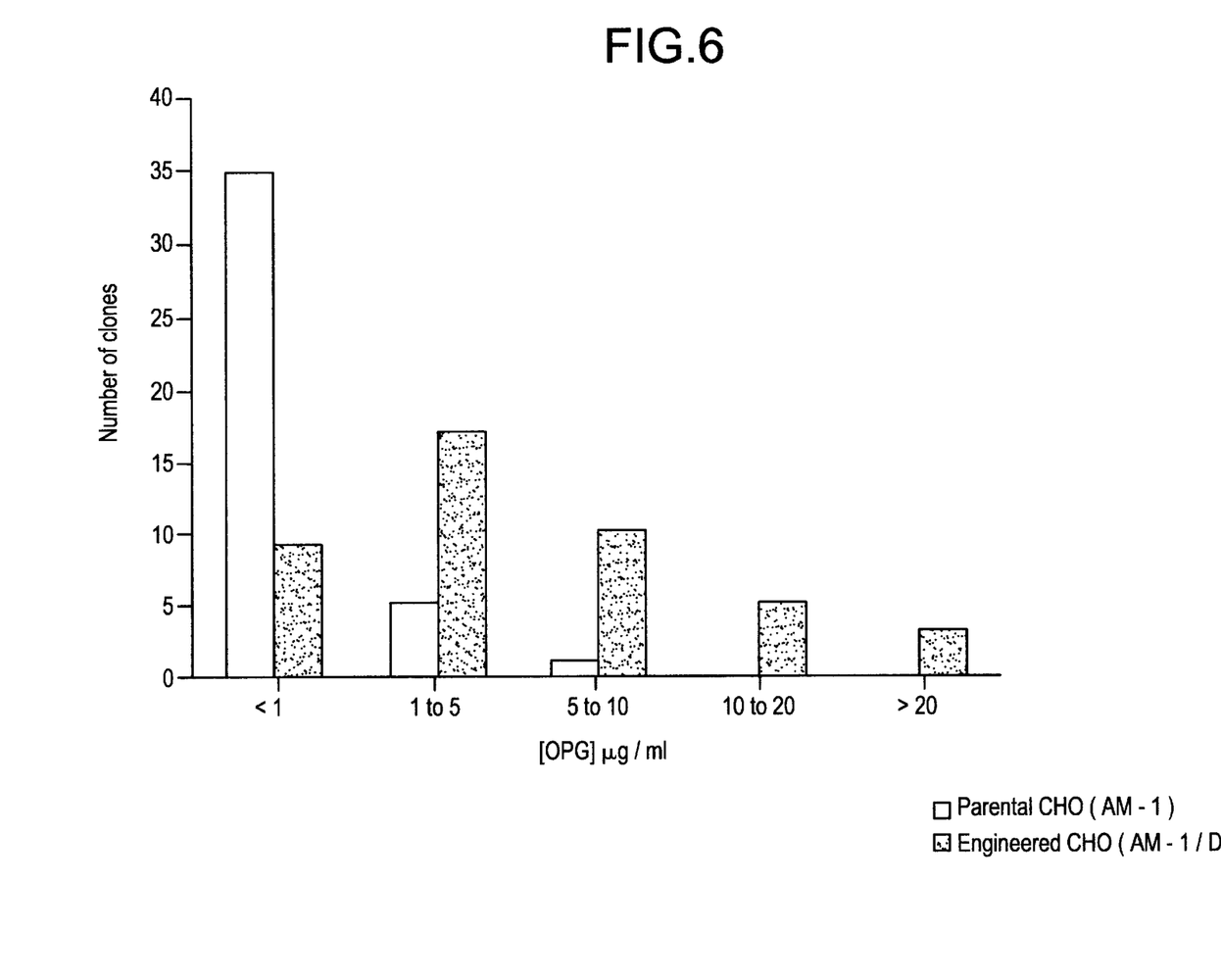
FIG. 6 shows a comparison of OPG(22-201)-Fc expression in the 24 highest expressing clones as previously determined by western blot. In each case, clones derived from the AM-1/cyclin D CHO cell line show significantly higher levels of expression of OPG(22-201)-Fc than clones derived from CHO(SF) cells.

Expression of two OPG constructs was compared in AM-1/cyclin D CHO cells and other CHO cell lines. OPG (22-201)-Fc was transfected into AM-1/cyclin D CHO cells and the parent CHO cell line, which had previously been adapted to growth in serum-free medium [CHO(SF)]. OPG (22–194).cys-Fc was transfected into AM-1 cyclin D CHO cells and into its parent AM-1 CHO cell line. The transfections were carried out using the standard calcium phosphate method and DHFR selection. Transfected colonies were isolated using glass cloning cylinders. Individual colonies were grown to confluence in 24-well plates. Serum-free conditioned medium harvests were analyzed for secreted OPG by western blot using a polyclonal antiserum against OPG. Conditioned medium samples from those clones showing the highest levels of expression by western blot were further analyzed by ELISA. We compared OPG(22-194)-cys-Fc expression levels in 46 individual clones derived from AM-1 CHO cells or AM-1/cycin D CHO cells (FIG. 5). We also compared OPG(22–201)-Fc expression in the 24 highest expressing clones as previously determined by western blot (FIG. 6). In each case, clones derived from the AM-1/cyclin D CHO cell line show significantly higher levels of expression than clones derived from CHO(SF) or AM-1 CHO cells.

Expression of NESP in Serum-Free Medium Adapted CHO cells

Figure 7:
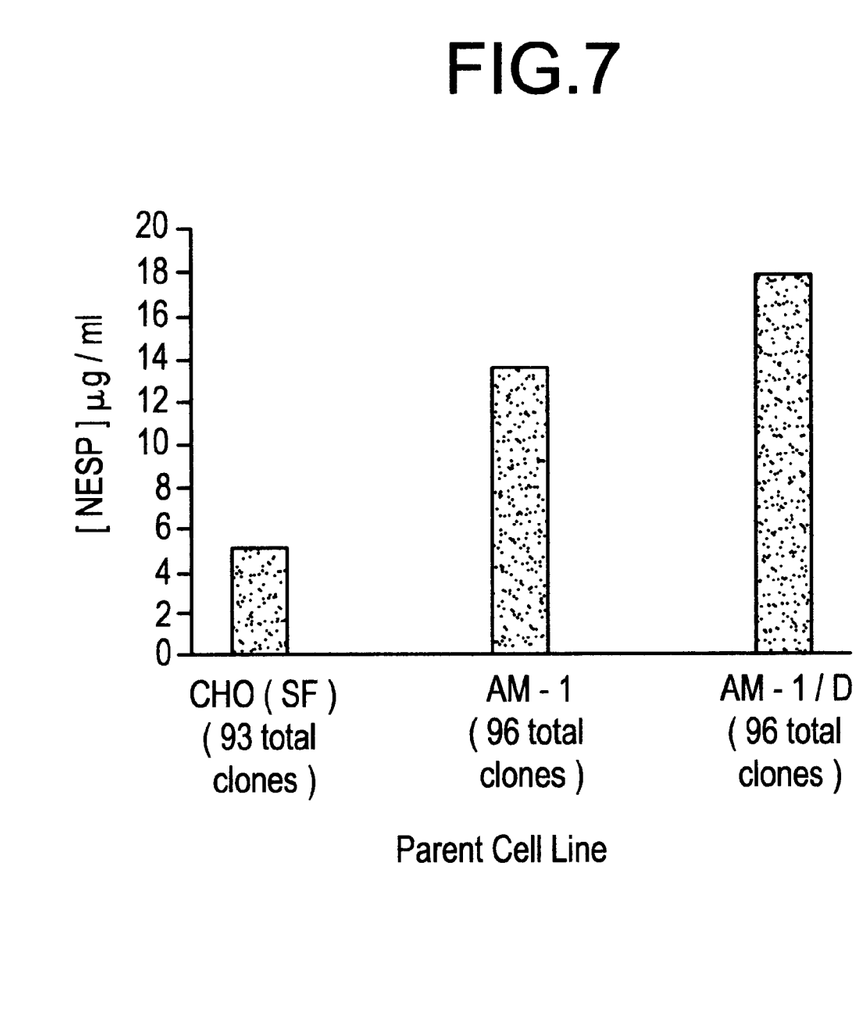
FIG. 7 shows average NESP expression determined by EIA in the 14 best clones derived from each parent CHO cell line. Conditioned medium samples were gathered from 24 well plates, 2 day harvest. Samples were pre-screened by western blot.
Figure 8A:
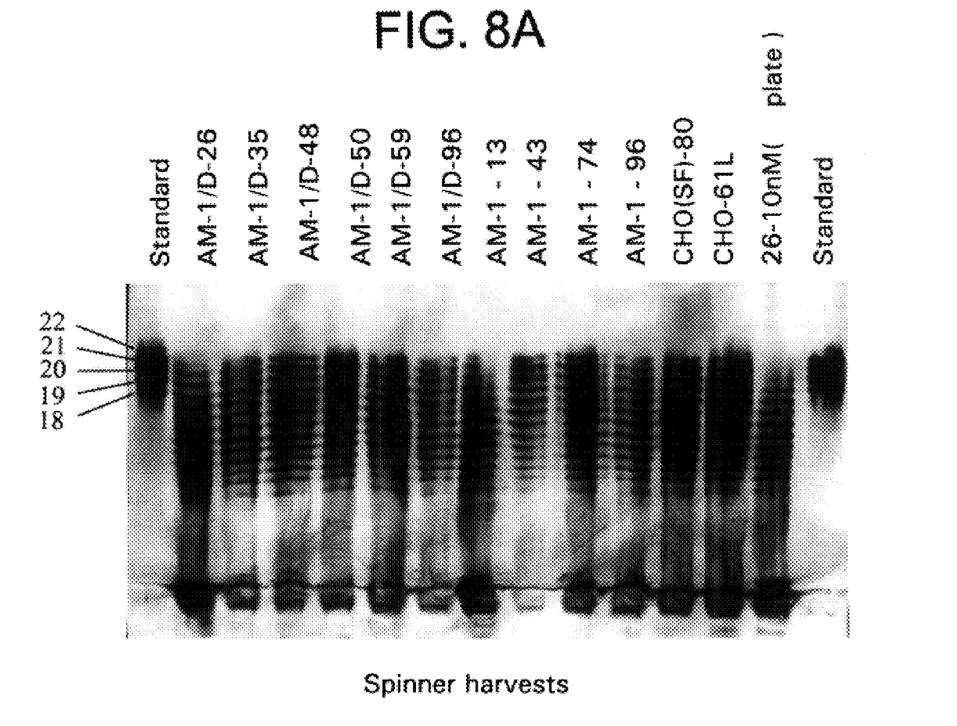
FIGS. 8A and 8B show IEF western blots of spinner and bioreactor harvests, comparing isoform distributions of secreted NESP protein from spinner and bioreactor cultures. Spinner harvests are from unamplified clones. The standard NESP protein, purified from roller bottle conditioned medium, shows the desired high molecular weight isoforms. The conditioned medium harvests contain all isoforms. The blots show the presence of high isoforms in all samples.
Figure 8B:
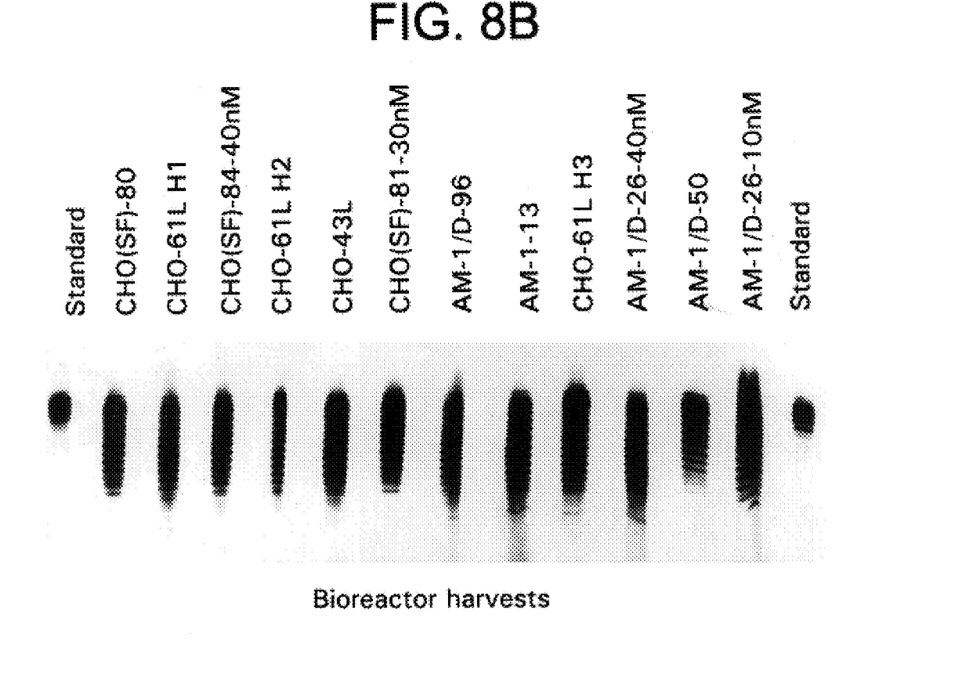

NESP DNA inserted into the pDSR.2 expression vector was transfected by the standard calcium phosphate method into three different serum-free adapted CHOd cell lines: CHOd-(SF), AM-1, and AM-1/cyclin D. The transfection, selection, and isolation of clones were carried out in serum-containing medium in adherent culture. Clones expressing high levels of NESP were initially identified by western blot using a monoclonal antibody to EPO. Quantitation of expression was done by EIA. The highest expressing clones from each cell line were tested for growth in suspension culture in serum-free medium. The clones also underwent DNA amplification by growth in gradually increasing concentrations of methotrexate in serum-containing medium in adherent culture. NESP expression during the amplification process was monitored by western blot and EIA analyses. At various stages during the amplification process, the clones were analyzed for growth and expression in serum-free suspension culture. Clones derived from the AM-1/cyclin D CHO cell line had an overall higher level of NESP expression than those derived from the other two parent CHO cell lines (FIG. 7). The clones were also analyzed by isoelectric focusing to determine isoform distribution. No significant differences were observed in the isoform distributions in the various clones or in a control cell line (61L) derived from the parent CHO cell line (FIGS. 8A and 8B).

Abbreviations used throughout this specification are defined as follows:

| | |
|---|---|
| CHO | Chinese hamster ovary |
| EBV | Epstein-Barr virus |
| EIA | enzyme immunoassay |
| EPO | erythropoietin |
| HBS | HEPES buffered saline |
| MTX | methotrexate |
| NESP | novel erythropoiesis stimulating protein |
| OPG | osteoprotegerin |

What is claimed is:

1. A mammalian cell comprising:
   a) an inserted gene construct for a cyclin D gene product, wherein the cyclin D gene product is functionally expressed in the cell at a level greater than the level of expression of said cyclin D gene product in the cell before said insertion; and
   b) an inserted gene construct for a protein of interest, wherein the protein of interest is expressed in the cell at a level greater than the level of expression of said protein of interest in the cell before said insertion.

2. The cell of claim 1 wherein the cell is a CHO cell.

3. The cell of claim 1 wherein the cell is an AM-1 cell.

4. The cell of claim 1 wherein the cyclin D gene product comprises a mammalian cyclin D1.

5. The cell of claim 1 wherein the cyclin D gene product comprises a human cyclin D.

6. The cell of claim 1 wherein the cyclin D gene product comprises a human cycin D1.

7. The cell of claim 1 wherein the protein of interest is an erythropoietin (EPO)-related protein, an osteoprotegerin (OPG)-related protein, or a leptin-related protein.

8. The cell of claim 1 wherein the protein of interest is EPO, Novel Erythropoiesis Stimulation Protein (NESP), OPG, OPG-Fc, leptin or Fc-leptin.

9. The cell of claim 2 wherein the cell is adapted to serum-free media.

10. A process for producing a protein of interest, which comprises:
    a) creating a mammalian cell that comprises
       1. an inserted gene construct for a cyclin D gene product wherein the cyclin D gene product is functionally expressed in the cell at a level greater than the level of expression of said cyclin D gene product in the cell before said insertion and
       2. an inserted gene construct for a protein of interest, wherein the protein of interest is functionally expressed in the cell at a level greater than the level of expression of said protein of interest in the cell before said insertion;
    b) culturing the cell under conditions permitting expression of the protein of interest and functional expression of the cyclin D gene product; and c) isolating the protein of interest.

11. The process of claim 10 wherein the cell is a CHO cell.

12. The process of claim 10 wherein the cell is an AM-1 cell.

13. The process of claim 10 wherein the cyclin D gene product comprises a mammalian cyclin D1.

14. The process of claim 10 wherein the cyclin D gene product comprises a human cyclin D.

15. The process of claim 10 wherein the cyclin D gene product comprises a human cyclin D1.

16. The process of claim 10 wherein the protein of interest is an EPO-related protein, an OPG-related protein, or a leptin-related protein.

17. The process of claim 10 wherein the protein of interest is EPO, NESP, OPG, OPG-Fc, leptin or Fc-leptin.

18. The process of claim 11 wherein the cell is adapted to serum-free media.

* * * * *

UNITED STATES PATENT AND TRADEMARK OFFICE
CERTIFICATE OF CORRECTION

PATENT NO. : 6,210,924 B1
DATED : April 3, 2001
INVENTOR(S) : Hu et al.

It is certified that error appears in the above-identified patent and that said Letters Patent is hereby corrected as shown below:

Column 1,
Line 46, change "MCB ,4" to -- MCB 14, --.

Column 2,
Line 39, change "pDSRαt2/OPG-Fc" to -- pDSRα2/OPG-Fc --.

Column 7,
Line 63, change "HO" to -- $H_2O$ --.

Column 11,
Line 21, change "MTW" to -- MTX --.

Signed and Sealed this

Fifth Day of February, 2002

JAMES E. ROGAN
Director of the United States Patent and Trademark Office

Attest:

Attesting Officer